United States Patent
Strickholm

(10) Patent No.: US 6,251,067 B1
(45) Date of Patent: Jun. 26, 2001

(54) MALE ERECTILE PROSTHESIS

(75) Inventor: Alfred Strickholm, Bloomington, IN (US)

(73) Assignee: Advanced Research & Technology Institute, Bloomington, IN (US)

( * ) Notice: Subject to any disclaimer, the term of this patent is extended or adjusted under 35 U.S.C. 154(b) by 0 days.

(21) Appl. No.: 09/338,738

(22) Filed: Jun. 23, 1999

(51) Int. Cl.[7] .................................................. A61F 5/00
(52) U.S. Cl. ................................................................ 600/39
(58) Field of Search ........................................ 600/38–41

(56) References Cited

U.S. PATENT DOCUMENTS

| | | | |
|---|---|---|---|
| 1,216,099 | * | 2/1917 | Falck ........................................ 600/39 |
| 2,254,915 | | 9/1941 | Sawyer . |
| 3,255,749 | | 6/1966 | Smithers . |
| 3,621,840 | | 11/1971 | Macchioni . |
| 3,633,572 | | 1/1972 | Wiggins . |
| 3,773,040 | | 11/1973 | Gavrilovich . |
| 4,724,829 | | 2/1988 | Knapps . |
| 5,085,209 | | 2/1992 | Gottschalk . |
| 5,221,251 | | 6/1993 | Edminster . |
| 5,246,015 | | 9/1993 | Baber . |
| 5,344,389 | | 9/1994 | Walsdorf et al. . |
| 5,360,390 | | 11/1994 | Maanum . |
| 5,522,787 | * | 6/1996 | Evans ........................................ 600/39 |
| 5,628,329 | | 5/1997 | Bennett et al. . |
| 5,667,471 | | 9/1997 | Weller et al. . |
| 6,015,379 | * | 1/2000 | Sachse ...................................... 600/39 |

* cited by examiner

Primary Examiner—Samuel G. Gilbert
(74) Attorney, Agent, or Firm—Baker & Daniels

(57) ABSTRACT

A method and apparatus for allowing a male with erectile dysfunction to participate in normal coitus is disclosed. A two piece device forms a male erectile prosthesis which can be utilized to allow a man with erectile dysfunction to participate in sexual activity. The prosthesis includes a penile wrap for providing rigidity to the penis and a thrust plate which is operable to provide resistance against any backward movement of the penis.

25 Claims, 2 Drawing Sheets

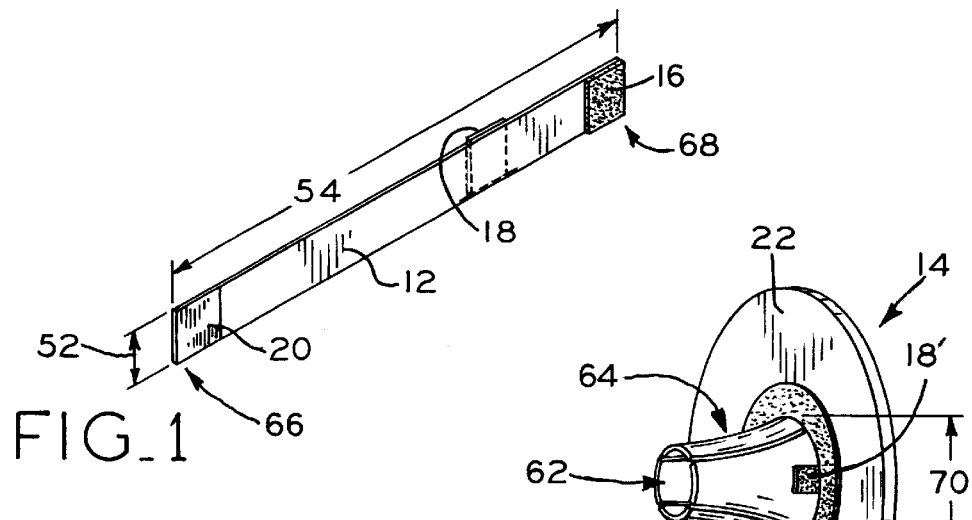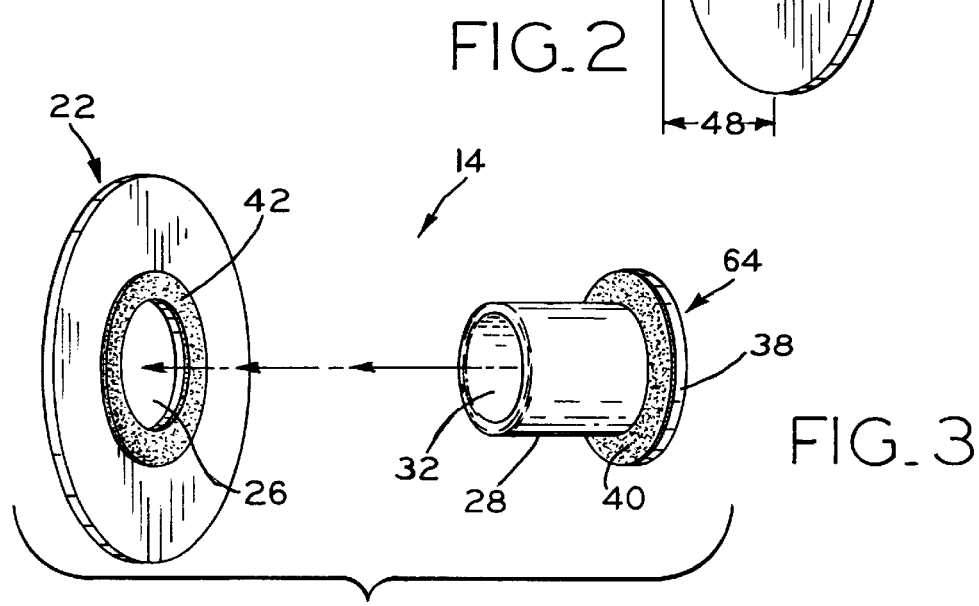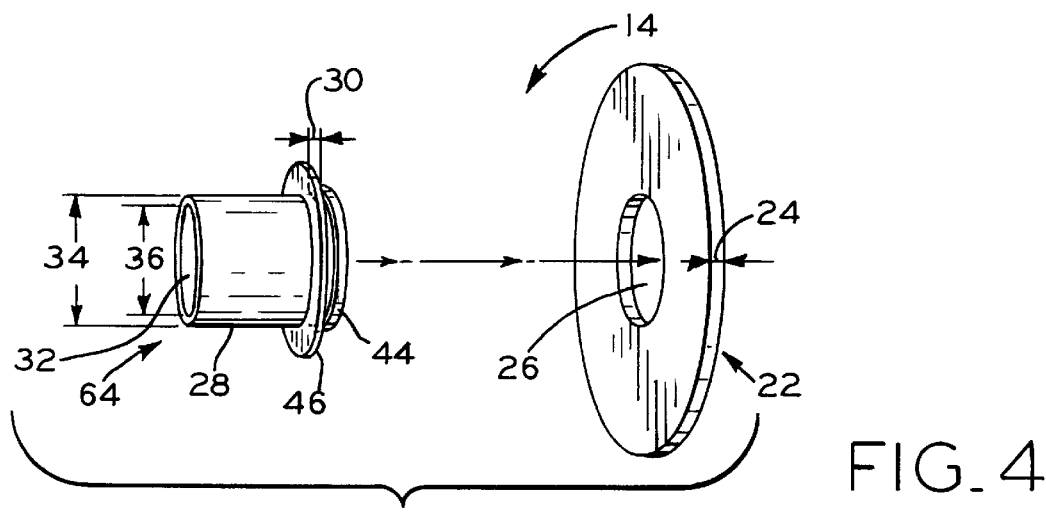

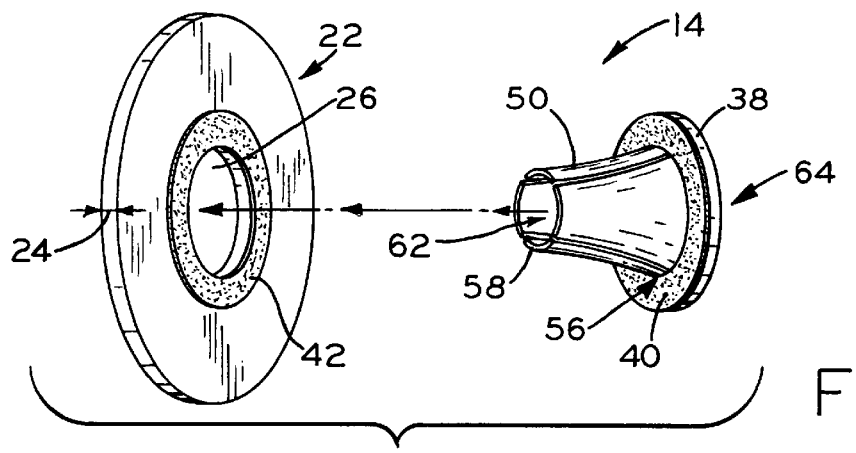
FIG_5
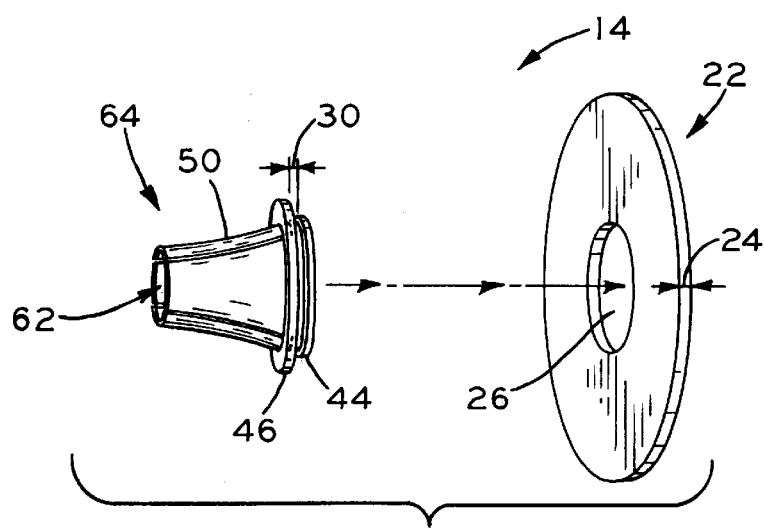
FIG_6
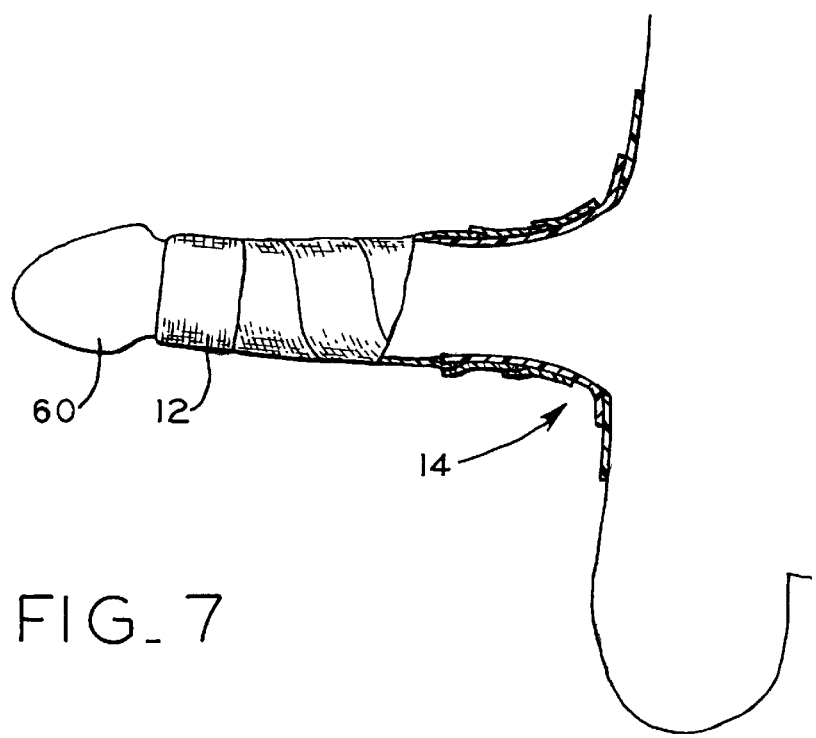
FIG_7

MALE ERECTILE PROSTHESIS

BACKGROUND OF THE INVENTION

1. Field of the Invention

The present invention relates to a method and apparatus which is useful to allow a man with erectile dysfunction to engage in sexual activity. Specifically, the current invention utilizes a prosthetic device designed to provide rigidity to the penis and to provide resistance against any backward movement of the penis.

2. Description of the Related Art

For a wide variety of reasons, many human males have erectile dysfunction. The problem of erectile dysfunction is wide spread. An estimated 10% of the male population of 10–20 million men are impotent in the United States.

Attempts to combat erectile dysfunction include the use of penile constrictor rings which are stretched over an erect penis and are designed to prevent blood from exiting the erect penis in an effort to maintain the erection. Use of these devices is limited to situations in which the man can achieve an erection and the devices can cause physical damage if left in place for an extended period of time.

Alternative attempts to combat erectile dysfunction include inflatable penile implants. Inflatable penile implants commonly utilize a pump located in the scrotum to inflate and deflate a balloon implanted in the penis. Receiving an inflatable penile implant is an expensive surgical procedure which many times does not produce acceptable results. These devices often fail and can cause ulceration and irreversible nerve and vascular damage as well as leading to further complications of penile function.

Vacuum devices have also been used to combat erectile dysfunction. These devices are designed to seal and lower the air pressure around a penis so that blood engorges the penis causing an erection. Vacuum type devices are commonly utilized in conjunction with constrictor rings so that the thusly obtained erection can be maintained. Vacuum devices are not uniformly successful and require significant time to be effectively utilized.

Various supporting devices have also been utilized to combat erectile dysfunction. These devices include support sleeves comprising one piece devices designed to fit around the penis. Many such support sleeves are difficult to attach and are additionally difficult to keep in place. Support sleeves do not provide resistance against backward movement of the penis.

In addition to support type devices, extension and other prosthetic type devices are available. However, these devices do not provide a satisfying sexual experience and are often only ornamental.

In addition to the above-mentioned efforts to combat erectile dysfunction, various pharmacological remedies are available. Pharmacological remedies include injectable drug solutions, urethral suppositories as well as oral pharmaceuticals.

Injectable pharmaceuticals work in only a certain number of cases and many times become ineffective after a few years of use. Injections require sterile needle handling by the patient and may lead to penile scarring. In addition to the requirements of sterile needle handling, these pharmaceuticals must be kept refrigerated, are expensive to purchase and cause discomfort in their method of application.

Urethral suppositories provide an alternative to injection. Urethral suppositories allow the pharmaceutical to be absorbed through the urethral wall into the penis and cause increased blood flow into the penis. Urethral suppositories do not work for everyone, must be kept refrigerated before use and are expensive.

Finally, oral pharmaceuticals may be employed to remedy erectile dysfunction. Oral pharmaceuticals currently available include VIAGRA. Oral pharmaceuticals are not uniformly effective and have side effects of varying degree. Side effects associated with oral pharmaceuticals utilized to combat erectile dysfunction include headache, facial flushing, nasal congestion, urinary tract infection, diarrhea, upset stomach and muscle aches in the pelvic area. Additionally, oral pharmaceuticals may produce extremely dangerous side effects in conjunction with other pharmaceuticals. For these reasons, extreme care must be taken when utilizing oral pharmaceuticals to combat erectile dysfunction.

What is needed in the art is a device which is effective to allow a man with erectile dysfunction to participate in sexual activity and which is free from the above-mentioned short comings of the currently available remedies for erectile dysfunction.

SUMMARY OF THE INVENTION

The present invention is directed to improve upon the currently available methods and apparatus for combating erectile dysfunction. Generally, a plate element having a sleeve is designed to fit against the pelvic region of a user, with the penis being placed in the sleeve. After the plate element is applied, a wrap element is utilized to wrap and provide rigidity to the penis. The wrap is applied starting just behind the glans and wrapping is completed when the sleeve of the thrust plate is covered.

Anatomical studies show that 9 portion (As 6/16/99) of the length of the erection extends into the body interior to provide rigidity to an erect penis and to resist backward movement of the penis during intercourse. Men with erectile dysfunction will not have this resistance to backward movement of the penis. The plate element of the current invention is specifically designed to work in conjunction with the wrap element to provide rigidity to the penis as well as resisting backward movement of the penis during intercourse.

The present invention utilizes a two part device to form a male erectile prosthesis. A penile wrap is provided which, when wrapped around the penis, will provide sufficient turgor for normal coitus. The second part of the current invention is a thrust plate having a sleeve. The thrust plate is designed to resist backward motion of the penis. The penis is placed through the thrust plate sleeve prior to being wrapped with the penile wrap. The penis is wrapped with the penile wrap starting just behind the glans and ending when the thrust plate sleeve has been covered. The penile wrap end covering the thrust plate sleeve is then affixed to the penile wrap and/or to the thrust plate sleeve so that the penile wrap is effectively affixed to the thrust plate and any backward motion of the supported penis is resisted.

The invention, in one form thereof, comprises a male erectile prosthesis which includes a penile wrap for wrapping and providing rigidity to a penis and an attaching means for securing the end of the penile wrap closest to the user's body. The penile wrap has a first end and a second end, with the first end designating the portion of the wrap distal from the body and the second end designating the portion of the wrap proximal to the body. The penile wrap is formed from an elastic material which may be coated with a rubber material, e.g. surgical rubber.

The invention, in another form thereof, comprises a male erectile prosthesis which includes a penile wrap for wrapping and providing rigidity to a penis and a thrust plate which is operable to provide resistance against any backward movement of the penis. An attaching means is utilized for securing the second end of the penile wrap to the thrust plate after the penile wrap is in place around the penis.

The invention, in another form thereof, comprises a male erectile prosthesis which includes a penile wrap for wrapping and providing rigidity to a penis. The penile wrap has a first end and a second end, and an attaching means for securing the second end of the penile wrap after the penile wrap is in place around the penis. In this form of the current invention, the attaching means comprises a first attaching member affixed to the second end of the penile wrap and a second attaching member for selectively engaging the first attaching member. The first and second attaching members can be, for example, mating pieces of hook and loop material such as VELCRO. The second attaching member can be affixed either to the thrust plate or to the penile wrap such that the second end of the penile wrap may be selectively engaged with the second attaching member. A color coded indicator may be utilized to designate the first end of the penile wrap.

The invention, in another form thereof, comprises an apparatus which is useful to allow a male with erectile dysfunction to engage in sexual activity. The apparatus of this form of the current invention includes rigidity means for providing rigidity to a penis. The rigidity means can be, for example, a penile wrap. A thrust plate forms a portion of the apparatus and provides resistance against backward movement of the penis. The thrust plate is selectively connected to the rigidity means.

The invention, in another form thereof, comprises a rigidity means for providing rigidity to a penis and a thrust plate which is selectively connected to the rigidity means and which is operable to provide resistance against any backward movement of the penis. In this form of the current invention, the thrust plate includes a first section having a first aperture. The first section of the thrust plate is formed of a rigid material and is curved to fit against the pelvic region at the base of the penis. The thrust plate further includes a second section having a second aperture. The second section is designed to surround the penis and is affixed to the first section. The first aperture is at least as large as the second aperture and the first and second apertures are concentric. The second section can be, for example, a slotted conical rubber sleeve.

The invention, in another form thereof, comprises rigidity means for providing rigidity to a penis and a thrust plate which is selectively connected to the rigidity means and which is operable to provide resistance against any backward movement of the penis. In this form of the current invention, the thrust plate includes a first section having a first aperture. The first section is curved to fit against the pelvic region at the base of the penis and is formed of a rigid material. The thrust plate further includes a second section having a second aperture. The second section is designed to surround the penis and the thrust plate includes attaching means for affixing the second section to the first section. The first aperture is at least as large as the second aperture and the first and second apertures are concentric when the second section is affixed to the first section. In one form of the current invention, the second section comprises a slotted conical rubber sleeve having a first end and a second end. The first and second ends are substantially circular, the first end is larger than the second end and the first end is selectively affixed to the first section of the thrust plate. The first end is not larger than the first aperture. Attaching means are used to affix the first end of the second section to the first section. The attaching means can be, for example, a single flange attaching configuration or a dual flange attaching configuration. In one form of the current invention, the second section has a height of one inch.

The invention, in another form thereof, comprises an apparatus useful to allow a man with erectile dysfunction to engage in sexual activity. The apparatus of this form of the current invention includes rigidity means for providing rigidity to a penis and a thrust plate which is operable to provide resistance against backward movement of the penis. The thrust plate is selectively connected to the rigidity means. The thrust plate includes a first section having a first aperture. The thrust plate is formed of a rigid material and is curved to fit against the pelvic region at the base of the penis. The thrust plate further includes a second section which has a second aperture and which is designed to surround the penis. The thrust plate in this form of the current invention further includes attaching means for affixing the second section to the first section. The first aperture is at least as large as the second aperture and the first and second apertures are concentric when the second section is affixed to the first section. In this form of the current invention, the second section of the thrust plate comprises a right circular cylinder having an outer diameter and an inner diameter. The outer diameter is not larger than the first aperture of the first section and the inner diameter is larger than the diameter of the penis of the intended user. In this form of the current invention, the attaching means can be, for example, a single flange configuration or a dual flange configuration.

The single flange configuration of the attaching means includes a flange affixed to the second section, which flange has a first attaching surface. The first section has a complimentary second attaching surface so that the first attaching surface and the second attaching surface are operable to selectively affix the second section to the first section. In the form of the current invention wherein the second section comprises a slotted conical rubber sleeve, the flange is affixed to the first end of the second section.

The dual flange configuration of the attaching means comprises a first flange affixed to the second section and a second flange affixed to the second section. The first section includes opposing sides which define a width. The first and second flanges are separated by a distance equal to the width of the first section, so that the second section and the first section can be connected by placing the second section through the first aperture such that the first flange and the second flange are adjacent the opposing sides of the first section. In the form of the current invention wherein the second section comprises a slotted conical rubber sleeve, the first flange is affixed to the first end of the second section.

The invention, in another form thereof, comprises a method of providing rigidity to a penis. This method includes the steps of: providing a penile wrap designed to provide rigidity to a penis and wrapping the penis with only the penile wrap. The step of wrapping the penis with the penile wrap may further include the steps of: identifying the starting end of the penile wrap; starting the wrap just behind the glans, using the starting end of the penile wrap; making sufficient wrap turns behind the glans to ensure that the glans is firmly held and cannot be forced back into the wrap; pulling the penis forward; continuing wrapping around the penis; discontinuing wrapping at the base of the penis; and securing the end of the wrap at the base of the penis.

The invention, in another form thereof, comprises a method of providing rigidity to a penis. This method includes the steps of: providing a thrust plate designed to resist backward movement of the penis, providing a device designed to provide rigidity to a penis, applying the rigidity device to provide rigidity to the penis, and affixing the rigidity device to the thrust plate so that backward movement of the penis is resisted.

The step of providing a device designed to provide rigidity to a penis may comprise providing a penile wrap and the step of applying the rigidity device to provide rigidity to the penis may comprise wrapping the penis with the penile wrap. The step of providing a thrust plate may comprise providing a thrust plate which includes a first portion that is curved to fit against the pelvic region at the base of the penis and a second portion designed to surround the penis. The step of wrapping the penis may further include the steps of: starting the wrap just behind the glans, making sufficient wrap turns behind the glans to ensure that the glans is firmly held and cannot be forced back into the wrap, pulling the penis forward, continuing wrapping around the penis and the portion of the thrust plate that surrounds the penis, discontinuing wrapping after reaching the portion of the thrust plate which is curved to fit against the pelvic region at the base of the penis, and securing the end of the wrap at the base of the penis.

An advantage of the present invention is the ability to provide a non-invasive penile prosthetic supporting device which provides sufficient penile support and turgor for normal coitus.

Another advantage of the present invention is the ability to provide a device which allows a man with erectile dysfunction to participate in normal coitus and which is designed to accommodate the physiological differences between men.

A further advantage of the present invention is the ability to provide a device which allows a man with any level of erectile dysfunction to participate in normal coitus.

Yet another advantage of the present invention is the ability to provide a device which effectively combats erectile dysfunction and which does not require a surgical procedure.

Another advantage of the present invention is the ability to effectively combat erectile dysfunction without experiencing the side effects which often accompany pharmacological remedies to erectile dysfunction.

Another advantage of the present invention is the ability to provide an erectile prosthesis which is designed to provide resistance against backward movement of the penis.

A further advantage of the present invention is that it is easy to use and generally requires less than a minute to apply.

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein:

FIG. 1 is a perspective view of the penile wrap of one form of the current invention;

FIG. 2 is a perspective view of an embodiment of the thrust plate of the current invention;

FIG. 3 is an exploded perspective view of an embodiment of the thrust plate of the-current invention;

FIG. 4 is an exploded perspective view of an embodiment of the thrust plate of the current invention;

FIG. 5 is an exploded perspective view of an embodiment of the thrust plate of the current invention;

FIG. 6 is an exploded perspective view of an embodiment of the thrust plate of the current invention; and FIG. 7 is a diagrammatic view of an application of the penile wrap/thrust plate combination.

Corresponding reference characters indicate corresponding parts throughout the several views. The exemplification set out herein illustrates one preferred embodiment of the invention, in one form, and such exemplification is not to be construed as limiting the scope of the invention in any manner.

DETAILED DESCRIPTION OF THE INVENTION

The present invention provides a male erectile prosthesis which allows a man with erectile dysfunction to participate in sexual activity. As generally illustrated in FIG. 7, penile wrap 12 is started behind glans 60 and wrapping continues until the base of the penis is reached. Prior to wrapping, the penis is inserted into thrust plate 14. Penile wrap 12 is affixed to thrust plate 14 so that rigidity is provided to the penis and backward motion of the penis is resisted.

FIG. 1 illustrates penile wrap 12 of the current invention. In one embodiment, penile wrap width 52 is approximately 1 ⅜ inches and penile wrap length 54 is approximately 20 inches. Various wrap sizes are acceptable and usable dimensions range from widths of approximately 1 inch to several inches while lengths range from approximately 8 inches to 24 inches. Penile wrap 12 is formed from highly elastic and soft material. Penile wrap 12 should be thin enough so that it may be easily applied. In one embodiment, penile wrap 12 is formed from a thin elastic coated with a soft surgical rubber.

Penile wrap 12 is advantageously formed from a soft material in an effort to eliminate vaginal discomfort. As explained above, penile wrap 12 can be formed from a highly elastic material which is subsequently coated with a soft surgical rubber. In another embodiment, penile wrap 12 is formed from a soft silk material so that the surgical rubber coating is unnecessary. Whether coated with surgical rubber or made from a soft silk material, penile wrap 12 may be easily cleaned and reused.

Penile wrap 12 is necessarily formed from highly elastic material so that the wrap may advantageously continue to provide rigidity to the penis as blood exits the penis and the penis collapses. Penile wrap 12 is advantageously formed so that it is elastic along length 54, but not width 52. If penile wrap 12 is elastic along width 52, the user could experience discomfort when the penis collapses and wrap length 54 decreases, causing a subsequent increase of wrap width 52.

As illustrated in FIG. 1, penile wrap 12 includes color indicator 20 which indicates first end 66 of penile wrap 12 as well as the surface of penile wrap 12 which is designed to be placed against the penis. In the embodiment illustrated in FIG. 1, penile wrap 12 includes first attaching member 16 and second attaching member 18. First attaching member 16 and second attaching member 18 can be, for example, complimentary or mating pieces of VELCRO. Additional fastening devices, including other hook and loop type fasteners may be utilized. Color indicator 20 signals the portion of penile wrap 12 which is to be placed closest to glans 60 (FIG. 7) when penile wrap 12 is wrapped about a penis. After wrapping is complete, first attaching member 16 and second attaching member 18 are utilized for securing second end 68 of penile wrap 12. Second attaching member 18 may be affixed to penile wrap 12 (FIG. 1) or to thrust plate 14 (FIG. 2). First attaching member 16 can thus be utilized to secure second end 68 of penile wrap 12 to either penile wrap 12 or thrust plate 14 depending upon whether second attaching member 18 is affixed to penile wrap 12 or thrust plate 14.

FIG. 2 illustrates an embodiment of the thrust plate of the current invention. Thrust plate 14 is formed from first section 22 and sleeve 50. In one embodiment, first section 22 is individually sized and molded to the body contour of the intended user. In the embodiment illustrated in FIG. 2, sleeve 50 is a slotted conical rubber sleeve. The sleeve is made of rubber to provide comfort to the user and the slotted conical configuration allows sleeve 50 to expand to accommodate the physiological differences in men. In one embodiment, sleeve 50 has a height 48 of approximately one inch. Sleeve 50 is affixed to first section 22 in this embodiment of thrust plate 14. Sleeve 50 is affixed to first section 22 so that sleeve 50 and first section 22 are concentric. As illustrated in FIG. 2, thrust plate 14 includes an opening 62 to accommodate a penis. In this embodiment of thrust plate 14, opening 62 is placed between the center and the peripherary of first section 22. In application, the portion of thrust plate 14 which corresponds to the shortest distance between the peripherary of first section 22 and sleeve 50 is placed closest to the underside of the penis of the wearer.

FIGS. 3 and 4 illustrate alternative embodiments of thrust plate 14. In the embodiments illustrated in FIGS. 3 and 4, thrust plate 14 is formed from first section 22 and second section 64. First section 22 is generally circular and includes first aperture 26. In the embodiment illustrated in FIG. 3, second section 64 includes right circular cylinder 28 and flange 38. Although a right cylindrical shape is depicted, other shapes may be utilized. Second aperture 32 traverses second section 64. Flange 38 includes first attaching surface 40. In this embodiment, first section 22 includes second attaching surface 42. First attaching surface 40 and second attaching surface 42 can be, for example, mating portions of hook and loop material such as VELCRO. First attaching surface 40 and second attaching surface 42 are operative to affix second section 64 to first section 22.

In the embodiment illustrated in FIG. 4, second section 64 includes right circular cylinder 28, first flange 44 and second flange 46. Right circular cylinder 28 includes inner diameter 36 and outer diameter 34. First flange 44 and second flange 46 are separated by distance 30. Distance 30 is substantially equal to width 24 of first section 22. In this embodiment, second section 64 is inserted into first aperture 26 of first section 22 such that first flange 44 and second flange 46 are adjacent opposing sides of first section 22 and hold second section 64 in place in relation to first section 22. The two piece thrust plate configuration is utilized so that second sections (64) of differing size may be utilized to accommodate the physiological differences in men and achieve a comfortable sizing for an individual user.

FIGS. 5 and 6 illustrate additional embodiments of thrust plate 14 which utilize a two piece configuration. In the embodiment illustrated in FIG. 5, thrust plate 14 is formed from first section 22 and second section 64. Second section 64 includes sleeve 50 and flange 38. Sleeve 50 has a first end 56 and a second end 58 and has a slotted conical configuration. First end 56 and second end 58 are substantially circular with first end 56 being larger than second end 58. Flange 38 includes a first attaching surface 40. First section 22 includes first aperture 26 and second attaching surface 42. First aperture 26 accommodates the insertion of second section 64. First attaching surface 40 and second attaching surface 42 are operable to affix first section 22 to second section 64.

In the embodiment illustrated in FIG. 6, thrust plate 14 is similarly formed from firs t section 22 and second section 64. Second section 64 includes sleeve d0, first flange 44 and second flange 46. First flange 44 and second flange 46 are separated by distance 30. Distance 30 is substantially equal to width 24 of first section 22. Second section 64 can be connected to first section 22 by placing second section 64 through first aperture 26 of first section 22 such that first flange 44 and second flange 46 are adjacent opposing sides of first section 22. Second section 64 of thrust plate 14 is contoured to comfortably fit the pelvic region at the base of the penis. In the configurations illustrated in FIGS. 4 and 6, a counter sunk region may be included in first section 22 of thrust plate 14 to accommodate first flange 44 and create a comfortable fit with the pelvic region of a user.

In operation, the penis is inserted through opening 62 (FIG. 2) of thrust plate 14. The appropriate thrust plate is selected so that the entry 70 of the thrust plate is larger than the user's penis. Penile wrap 12 is then put in place. First end 66 of penile wrap 12 (FIG. 1) is placed just behind glans 60 (FIG. 7). one or two turns are made behind glans 60 to ensure that glans 60 is held firmly and cannot be forced back into penile wrap 12. Penile wrap 12 is then worked back and the penis is pulled forward to provide maximum extension. Wrapping concludes when first section 22 of thrust plate 14 has been reached. Second end 68 of penile wrap 12 is then secured to either thrust plate 14 or penile wrap 12, depending upon which embodiment is utilized, i.e. whether second attaching member 18 is affixed to penile wrap 12 or to thrust plate 14. Penile wrap 12 provides rigidity to the penis, while thrust plate 14 provides resistance to backward movement of the penis. A condom may be placed over the prosthesis for safe sex usage. Penile wrap 12 and/or thrust plate 14 may advantageously be utilized in conjunction with known erectile dysfunction remedies such as, constrictor rings, vacuum devices and pharmacological remedies. In cases where known erectile dysfunction remedies are not completely successful, penile wrap 12 and/or thrust plate 14 will provide an effective supplement to these remedies allowing the user to participate in normal coitus. Penile wrap 12 is designed so that wrapping should begin behind glans 60. In this way, the most sensitive portion of the penis is exposed during sexual activity so as to provide a satisfying sexual experience for the user. Depending upon the extent of erectile dysfunction, penile wrap 12 may be effective without the use of thrust plate 14. Thrust plate 14 may advantageously be utilized in conjunction with penile wrap 12 depending upon the level of erectile dysfunction experienced by the user.

The measured penile collapse turgor or buckling pressure with the prosthesis of the current invention exceeds 760 mm Hg under forward thrust. As 100 mm Hg is considered sufficient for normal coitus, the invention is successful in allowing those with poor penile erectile turgor and/or dysfunction to participate in normal coitus.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A male erectile prosthesis, comprising:
 a penile wrap for wrapping and providing rigidity to a penis, said penile wrap having a first end, a second end, and a width:

an attaching means for securing said second end of said penile wrap after the penile wrap is in place;

wherein said width of said penile wrap is sized whereby wrapping of the penis requires at least two successive turns of said penile wrap about the penis; and a thrust plate, said thrust plate being operable to provide resistance against any backward movement of the penis, said attaching means selectively attaching said second end of said penile wrap to said thrust plate.

2. The male erectile prosthesis of claim 1, wherein said attaching means comprises:

a first attaching member, said first attaching member affixed to said second end of said penile wrap; and a second attaching member affixed to one of said penile wrap and said thrust plate, wherein said second attaching member selectively engages said first attaching member.

3. The male erectile prosthesis of claim 2, wherein said second attaching member is affixed to said thrust plate.

4. The male erectile prosthesis of claim 2, wherein said second attaching member is affixed to said penile wrap.

5. The male erectile prosthesis of claim 1, wherein said width of said penile wrap is approximately 3 centimeters (1.18 inches).

6. The male erectile prosthesis of claim 1 wherein said penile wrap comprises an elastic material.

7. The male erectile prosthesis of claim 1, wherein said penile wrap comprises:

an elastic material; and a rubber material, said rubber material coating said elastic material.

8. A male erectile prosthesis, comprising:

a penile wrap for wrapping and providing rigidity to a penis, said penile wrap having a first end, a second end, and a width; and an attaching means for securing said second end of said penile wrap after the penile wrap is in place;

wherein said width of said penile wrap is sized whereby wrapping of the penis requires at least two successive turns of said penile wrap about the penis;

wherein said penile wrap further comprises a color indicator designating said first end of said penile wrap.

9. An apparatus useful to allow a man with erectile dysfunction to engage in sexual activity, said apparatus comprising:

a penile wrap for wrapping and providing rigidity to a penis, said penile wrap having a width; and a thrust plate, said thrust plate being operable to provide resistance against any backward movement of the penis, said thrust plate selectively connected to said penile wrap;

wherein said width of said penile wrap is sized whereby wrapping of the penis requires at least two successive turns of said penile wrap about the penis.

10. The apparatus as recited in claim 9, wherein said thrust plate comprises:

a first section having a first aperture, said first section being curved to fit against the pelvic region at the base of the penis, said first section being formed of a rigid material; and a second section having a second aperture, said second section surrounding the penis, said first aperture being at least as large as said second aperture, said second section affixed to said first section, said second aperture and said first aperture being concentric.

11. The apparatus as recited in claim 10, wherein said second section comprises a slotted conical rubber sleeve, said slotted conical rubber sleeve having a first end and a second end, said first end and said second end being substantially circular, said first end being larger than said second end, said first end being affixed to said first section.

12. The apparatus as recited in claim 11, wherein said second section has a height of one inch.

13. The apparatus as recited in claim 9, wherein said thrust plate comprises:

a first section having a first aperture, said first section being formed of a rigid material, said first section being curved to fit against the pelvic region at the base of the penis;

a second section having a second aperture, said second section surrounding the penis, said first aperture being at least as large as said second aperture; and attaching means for affixing said second section to said first section, wherein said second aperture and said first aperture are concentric when said second section is affixed to said first section.

14. The apparatus as recited in claim 13, wherein said second section comprises a right circular cylinder, said second section having an outer diameter and an inner diameter, said outer diameter being no larger than said first aperture, said inner diameter being larger than the diameter of the penis of the user.

15. The apparatus as recited in claim 14, wherein said attaching means comprises:

a flange, said flange affixed to said second section, said flange having a first attaching surface, said first section having a second attaching surface, wherein said first attaching surface and said second attaching surface are operable to selectively affix said second section to said first section.

16. The apparatus as recited in claim 14, wherein said attaching means comprises:

a first flange, said first flange affixed to said second section; and a second flange, said second flange affixed to said second section, said first section having opposing sides defining a width, said first flange and said second flange being separated by a distance equal to said width of said first section, whereby said second section and said first section are connected by placing said second section through said first aperture such that said first flange and said second flange are adjacent said opposing sides of said first section.

17. The apparatus as recited in claim 13, wherein said second section comprises a slotted conical rubber sleeve, said slotted conical sleeve having a first end and a second end, said first end and said second end being substantially circular, said first end being larger than said second end, said first end being no larger than said first aperture.

18. The apparatus as recited in claim 17, wherein said attaching means comprises:

a flange, said flange affixed to said first end of said second section, said flange having a first attaching surface, said first section having a second attaching surface, wherein said first attaching surface and said second attaching surface are operable to selectively affix said second section to said first section.

19. The apparatus as recited in claim 17, wherein said attaching means comprises:

a first flange, said first flange affixed to said first end of said second section; and a second flange, said second flange affixed to said second section, said first section having opposing sides defining a width, said first flange and said second flange being separated by a distance equal to said width of said first section, whereby said second section and said first section are connected by placing said second section through said first aperture such that said first flange and said second flange are adjacent said opposing sides of said first section.

20. The male erectile prosthesis of claim 9, wherein said width of said penile wrap is approximately 3 centimeters (1.18 inches).

21. A method of providing rigidity to a penis, comprising:
providing a penile wrap for wrapping and providing rigidity to a penis, said penis having a length, said penile wrap having a width sized whereby wrapping of the penis requires at least two successive turns of said penile wrap about the penis; and
wrapping the penis with the penile wrap in a helical fashion along the length of the penis.

22. A method of providing rigidity to a penis, comprising:
providing a penile wrap for wrapping and providing rigidity to a penis, said penile wrap having a width sized whereby wrapping of the penis requires at least two successive turns of said penile wrap about the penis; and
wrapping the penis with the penile wrap;
wherein said step of wrapping the penis comprises:
identifying the starting end of the penile wrap;
starting the wrap just behind the glans, using the starting end of the penile wrap;
making sufficient wrap turns behind the glans to ensure that the glans is firmly held and cannot be forced back into the wrap;
pulling the penis forward;
continuing wrapping around the penis; discontinuing wrapping at the base of the penis; and
securing the end of the wrap at the base of the penis.

23. A method of providing rigidity to a penis, comprising:
providing a thrust plate designed to resist backward movement of the penis;
providing a penile wrap for wrapping and providing rigidity to a penis, said penile wrap having a width sized whereby wrapping of the penis requires at least two successive turns of said penile wrap about the penis;
wrapping the penis with the penile wrap; and
affixing the penile wrap to the thrust plate so that backward movement of the penis is resisted.

24. The method of claim 23, wherein said step of providing a thrust plate comprises providing a thrust plate which includes a first portion that is curved to fit against the pelvic region at the base of the penis and a second portion designed to surround the penis.

25. The method of claim 23, wherein said step of wrapping the penis comprises:
starting the wrap just behind the glans;
making sufficient wrap turns behind the glans to ensure that the glans is firmly held and cannot be forced back into the wrap;
pulling the penis forward;
continuing wrapping around the penis and the portion of the thrust plate that surrounds the penis;
discontinuing wrapping after reaching the portion of the thrust plate which is curved to fit against the pelvic region at the base of the penis; and
securing the end of the wrap at the base of the penis.

* * * * *